United States Patent

Sakai et al.

[11] Patent Number: 6,100,219
[45] Date of Patent: Aug. 8, 2000

[54] PLANT GROWTH ACCELERATOR

[75] Inventors: Kunikazu Sakai, Tokyo; Yasuo Kamuro, Aichi; Hiroki Kuriyama, Kanagawa, all of Japan

[73] Assignees: Sagami Chemical Research Center; Tama Biochemical Co., Ltd.; Bal Planning Co., Ltd., all of, Japan

[21] Appl. No.: 09/117,937

[22] PCT Filed: Feb. 7, 1997

[86] PCT No.: PCT/JP97/00315

§ 371 Date: Nov. 30, 1998

§ 102(e) Date: Nov. 30, 1998

[87] PCT Pub. No.: WO97/28690

PCT Pub. Date: Aug. 14, 1997

[30] Foreign Application Priority Data

Feb. 8, 1996 [JP] Japan ..................................... 8-022198

[51] Int. Cl.⁷ ............................ A01N 43/16; A01N 43/20
[52] U.S. Cl. .......................................................... 504/140
[58] Field of Search .............................................. 504/140

[56] References Cited

U.S. PATENT DOCUMENTS 5,518,995  5/1996  Abrams et al. ........................ 504/348

FOREIGN PATENT DOCUMENTS

WO91/02728  3/1991  WIPO ........................... C07D 303/38
WO96/08481  3/1996  WIPO ........................... C07D 303/40

OTHER PUBLICATIONS

Sakai, K., et al; *Convenient Synthesis of Optically Active Abscisic Acid and Xanthoxin*, Tetrahedron, vol. 48, No. 38 pp. 8229–8238 (1992).

*Primary Examiner*—S. Mark Clardy
*Attorney, Agent, or Firm*—Limbach & Limbach LLP

[57] ABSTRACT

The present invention provides a plant growth promoter comprising an epoxycylohexane derivative represented by the general formula:

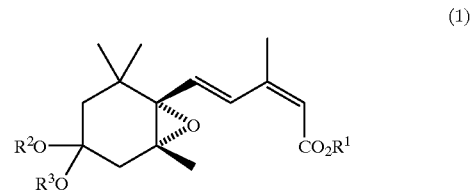

(1)

(wherein by $R^1$ represents a hydrogen atom, C1 to C6 alkyl group or C3 to C6 cycloalkyl group, and $R^2$ and $R^3$ are independently lower alkyl groups or are combined to form a polymethylene group which may be substituted with an alkyl group) and gibberellin as active ingredients.

7 Claims, No Drawings

PLANT GROWTH ACCELERATOR

TECHNICAL FIELD

The present invention relates to a plant growth promoter and in particular to plant growth stimulation of vegetables, root crops, potatoes, fruit vegetables, fruits, grains, flowers and grasses, and crops for special uses, etc. The growth promotion refers to growth of leaves and roots, promotion of flowering, promotion of thickening of potatoes and fruits, and increase in the quantity of fruit.

BACKGROUND ART

A major problem in agricultural technology is the improvement and stabilization of production. For this purpose, many plant growth promoters have already been developed. However, the effects of conventional promoters are limited, and the need remains for an agent that more efficiently causes stable effects For example, gibberellin is a plant hormone and is applied as a plant growth promoter to a large number of crops, yet is limited in effect as well as in the range of applicable crops.

It is also known that combinations of gibberellin and natural abscisic acid, are possible to promote plant growth such as promotion of thickening and growth of crops, promotion of elongation of cedars, promotion of flowering etc. However, the concentration of each chemical necessary to yield an effect is high, so development of more superior plant growth promoters has been desired (Japanese Laid-Open Patent Publication No. 139912/1993; Japanese Laid-Open Patent Publication No. 172110/1994; Gifu University, Local Joint Research Center, Report No. 5, pp. 81–86, May 1995).

DISCLOSURE OF THE INVENTION

The present invention provides a plant growth promoter comprising an epoxycylohexane derivative represented by the general formula:

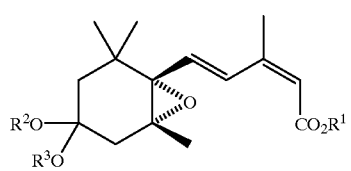

(1)

(wherein $R^1$ represents a hydrogen atom, C1 to C6 alkyl groups or C3 to C6 cycloalkyl groups, and $R^2$ and $R^3$ are independently lower alkyl groups or are combined to form a polymethylene group which may be substituted with an alkyl group) and gibberellin as active ingredients.

BEST MODE FOR CARRYING OUT THE INVENTION

The C1 to C6 alkyl groups represented by $R^1$ in the general formula (1) include a methyl group, ethyl group, propyl group, isopropyl group, butyl group, isobutyl group, s-butyl group, t-butyl group, pentyl group, isopentyl group, hexyl group, s-hexyl group etc. Among these, C2 to C4 groups are preferable for physiological action, and particularly a propyl group or isopropyl group are preferable.

The C3 to C6 cycloalkyl groups represented by $R^1$ in the general formula (1) include a cyclopropyl group, cyclobutyl group, cyclopentyl group and cyclohexyl group.

The lower alkyl groups represented by $R^2$, $R^3$ in the general formula (1) are preferably C1 to C4 straight-chain alkyl groups, specifically methyl group, ethyl group, propyl group and butyl group. The polymethylene group which may be substituted with an alkyl group include C2 to C6 groups, specifically ethylene group, propylene group, trimethylene group etc. Among these, the ethylene group is preferable for its high activity and easy synthesis.

In general, the epoxycyclohexane derivative of the general formula (1) used in the present invention is obtained in the following manner:

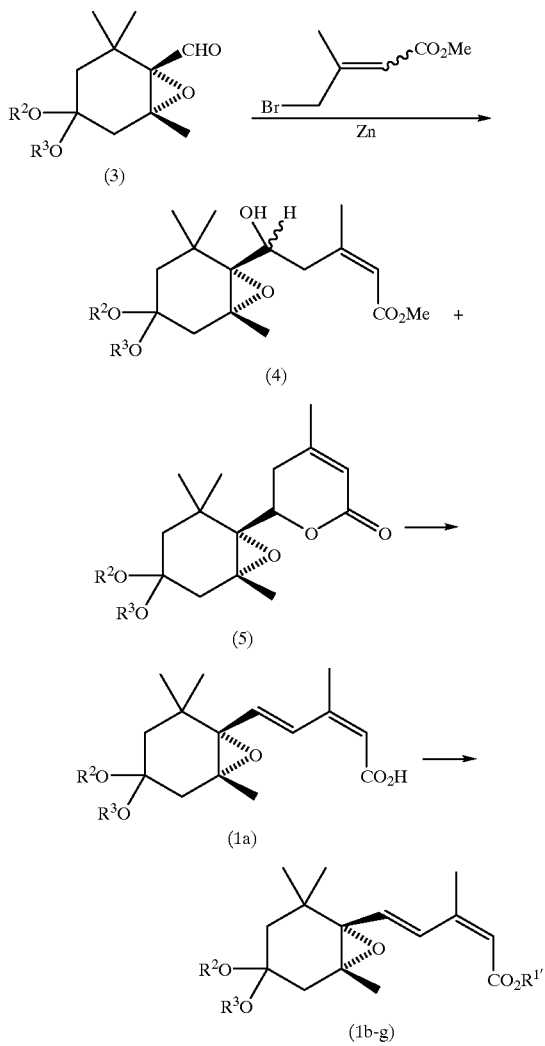

wherein $R^{1'}$ represents C1 to C6 alkyl groups or C3 to C6 cycloalkyl groups, and $R^2$ and $R^3$ have the same meaning as defined above.

The starting material, epoxycyclohexane carbaldehyde (3) can be synthesized by a method described in the literature (see for example, Helv. Chim. Acta, 71, 931 (1988)). Conversion of Compound (3) into the carboxylic acid of the general formula (1a) can be carried out according to the method described in Japanese Laid-Open Patent Publication No. 184966/1991. Further, Compound (1a) can be synthesized wherein $R^1$ is a methyl group by allowing diazomethane to act on (1a) as described in Japanese Patent Laid-Open Patent Publication No. 184966/1991. In general, the ester compounds represented by general formula (1) can be obtained, for example, by esterification of the carboxylic acid (1a), using e.g. a method of reacting it with a corresponding alcohol in the presence of a condensation agent such as carbodiimide.

Although the gibberellin used in the present invention may be any gibberellin, insofar as it has plant growth action, gibberellin $A_3$ ($GA_3$), gibberellin $A_4$ ($GA_4$), gibberellin $A_7$ ($GA_7$) in particular are preferably used for their effect.

The particular plant growth promoter of the present invention for a given use will have an epoxycyclohexane derivative and a gibberellin type as determined by for example the type of subject plant, the application form, application method, and time of application. In the case where the plant growth promoter is sprayed in the form of a solution, both the epoxycyclohexane derivative and gibberellin advantageously are in the concentration range of 500 to 0.01 ppm, preferably 50 to 0.05 ppm, and more preferably 10 to 0.1 ppm. All "epoxycyclohexane" or "gibberellin" compounds as termed herein refers not only to a single compound but each term may represent a mixture of compounds that are classified as be epoxycyclohexanes or gibberellins respectively.

A composition of the growth promoter of the present invention can contain, for example, conventionally used carriers, emulsifiers, dispersants, spreaders, sticking agents and disintegrating agents.

A plant growth regulator according to the present invention can be applied to plants or to a field seeded with plants, for example, in the form of a powder, emulsion, wettable powder, or granules, after preparation by mixing said epoxycyclohexane derivative and a steroid from brassica (i.e. gibberellin) with, for example, a conventional carrier or diluent. Further, they can be mixed with other plant growth regulators known in the art or with a weed killer, microbicide, insecticide, or the like. Further, additives such as, for example, spreaders, emulsifiers, wetting agents, dispersants, sticking agents, disintegrating agents may be included. In selecting a suitable carrier, diluent, additive or the like, those rendering the plant growth regulating action most effective are preferred.

The invention advantageously is used with a target plant such as, for example, a vegetable such as spinach, Chinese cabbage, cucumber, eggplant, beefsteak plant, cabbage, garland chrysanthemum, leek or the like, a root crop such as radish, sweet potato, potato, onion etc., grains such as rice, wheat, corn or the like, a bean such as soybean, adzuki bean, peanut or the like, a crop for special use such as beet, sugarcane, hemp or the like, a fruit such as grape, tangerine, persimmon, apple, tomato, melon, pear, strawberry, peach, banana, pineapple or the like, coffee, an ornamental plant such as a rubber tree, phoenix, Benjamin or the like, and a flower such as chrysanthemum, carnation, rose, bellflower, lily, tulip or the like.

Hereinafter, the present invention is described in more detail with reference to Synthesis Examples and Test Examples, which, however, are not intended to limit the present invention.

EXAMPLES

Synthesis Example

Synthesis of (1d)

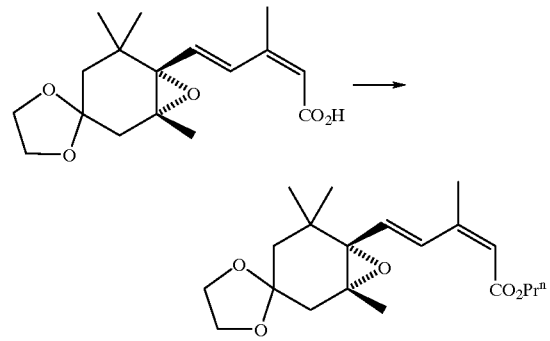

98 mg (0.80 mmol) of p-dimethylaminopyridine (DMAP) were added to a solution of 308 mg (1.00 mmol) of 4,4-ethylenedioxy-1-{4-(hydroxycarbonyl)-3-methyl-1,3-butadiene-1-yl}-1,2-oxo-2,6,6-trimethylcyclohexane (1a) (a product obtained in the same manner as in Example 2 in Japanese Laid-Open Patent Publication No. 184966/1991) and 180 mg (224 μL, 3.00 mmol) of propyl alcohol in dry dichloromethane (1.5 mL) and coaled in an argon atmosphere. A solution of 227 mg (1.10 mmol) of dicyclohexyl carbodiimide in dichloromethane (10 mL) was added thereto over the period of 5 minutes with stirring under cooling on ice, and the mixture was stirred as such for 15 minutes and further at room temperature for 3 hours. After treatment in a usual manner, 385 mg of the crude oily matter thus obtained was purified by chromatography on a silica gel column to give 296 mg of 4,4-ethylenedioxy-1-{4-(propoxycarbonyl)-3-methyl-1,3-butadiene-1-yl}-1,2-oxo-2,6,6-trimethylcyclohexane (1d) as colorless oily matter (yield 84%)

$^1$H-NMR(CDCl$_3$) δ (ppm): 0.96(3H, t, J=7.4), 1.00(3H, s), 1.22(3H, s), 1.25(3H, s), 1.34(1H, dd, J=2.1, 13.6), 1.68(2H, dd, J=6.7, 7.4), 1.74(1H, d, J=13.6), 2.01(3H, d, J=1.3), 2.04(1H, dd, J=2.1, 15.7), 2.28(1H, d, J=15.7), 3.81~3.97(4H, m), 4.07(2H, d, J=6.7), 5.71(1H, brs), 6.27 (1H, dd, J=0.6, 16.1), 7.62(1H, dd, J=0.7, 16.1).

LRMS m/z: 350(M$^+$), 291(M$^+$—C$_3$H$_7$O), 264(M$^+$—C$_4$H$_6$O$_2$).

HRMS m/z: Theoretical, 350.2092 (as C$_{20}$H$_{30}$O$_5$); Found, 350.2103

$[\alpha]_D^{20}$=10.22 (c 1.8, CHCl$_3$)

Synthesis Example 2

Synthesis of (1c)

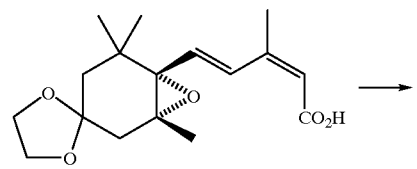

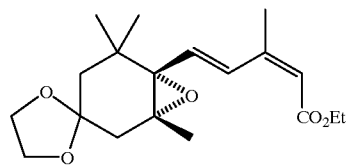

4,4-Ethylenedioxy-1-{4-(ethoxycarbonyl)-3-methyl-1,3-butanediene-1-yl}-1,2-oxo-2,6,6-trimethylcyclohexane (1c), 264 mg (yield 78.5%), was obtained in the same manner in Synthesis Example 1 except that 138 mg (3.00 mmol) of ethyl alcohol was used in place of propyl alcohol.

$^1$H-NMR(CDCl$_3$) δ (ppm): 1.00(3H, s), 1.22(3H, s), 1.25 (3H, s), 1.38(3H, t, J=7.1), 1.34(1H, dd, J=2.1, 13.7), 1.75 (1H, d, J=13.7), 2.01(3H, d, J=1.3), 2.05(1H, dd, J=2.1, 15.7), 2.28(1H, d, J=15.7), 3.82~3.96(4H, m), 4.17(2H, q, J=7.1), 5.70(1H, brs), 6.27(1H, dd, J=0.6, 16.0), 7.63(1H, dd, J=0.8, 16.0).

LRMS m/z: 336(M$^+$).

HRMS m/z: Theoretical, 336.1935 (as C$_{19}$H$_{28}$O$_5$); Found, 336.1913

Synthesis Example 3

Synthesis of (1e)

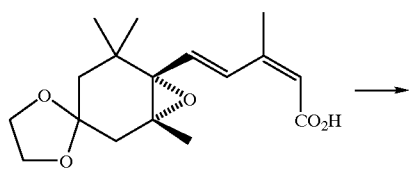

4,4-Ethylenedioxy-1-{4-(isopropoxycarbonyl)-3-methyl-1,3-butanediene-1-yl}-1,2-oxo-2,6,6-trimethylcyclohexane (1e), 282 mg (yield 81%). was obtained in the same manner in Synthesis Example 1 except that 180 mg (230 μl) of isopropyl alcohol was used in place of propyl alcohol.

$^1$H-NMR(CDCl$_3$) δ (ppm): 1.00(3H, s), 1.22(3H, s), 1.25 (3H, s), 1.26(6H, d, J=6.3), 1.34(1H, dd, J=2.1, 13.7), 1.74(1H, d, J=13.7), 2.00(3H, d, J=1.3), 2.04(1H, dd, J=2.1, 15.8), 2.28(1H, d, J=15.8), 3.81~3.94(4H, m), 5.06(1H, sept, J=6.3), 5.68(1H, brs), 6.26(1H, dd, J=0.6, 16.1), 7.61(1H, dd, J=0.7, 16.1).

LRMS m/z: 350(M$^+$), 291(M$^+$—C$_3$H$_7$O), 264(M$^+$—C$_4$H$_6$O$_2$).

HRMS m/z: Theoretical, 350.2091 (as C$_{20}$H$_{30}$O$_5$); Found, 350.2087

$[α]_D^{20}$=13.00 (c 1.8, CHCl$_3$)

Synthesis Example 4

Synthesis of (1f)

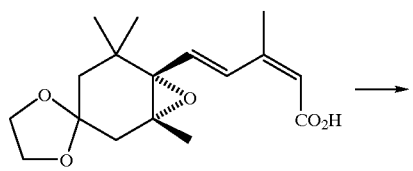

4,4-Ethylenedioxy-1-{4-(butoxycarbonyl)-3-methyl-1,3-butanediene-1-yl}-1,2-oxo-2,6,6-trimethylcyclohexane (1f), 306 mg (yield 84%), was obtained in the same manner in Synthesis Example 1 except that 227 mg (3.00 mmol) of butyl alcohol was used in place of propyl alcohol.

$^1$H-NMR(CDCl$_3$) δ (ppm): 0.94(3H, t, J=7.4), 1.00(3H, s), 1.22 (3H, s), 1.25 (3H, s), 1.34 (1H, dd, J=2, 1, 13.7) 1.40(2H, tq, J=7.4, 7.4), 1.64(2H, tt, J=6.7, 7.4), 1.74(1H, d, J=13.7), 2.01(3H, d, J=1.2), 2.04(1H, dd, J=2.1, 15.1), 2.28(1H, d, J=15.7), 3.82~3.96(4H, m), 4.12(2H, t, J=6.7) 5.70(1H, brs), 6.27(1H, dd, J=0.5, 16.0), 7.63(1H, dd, J=0.7, 16.0), LRMS m/z: 364(M$^+$).

HRMS m/z: Theoretical, 364.2247 (as C$_{11}$H$_{32}$O$_5$); Found, 364.2253

Synthesis Example 5

Synthesis of (1g)

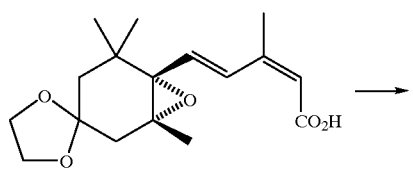

4,4-Ethylenedioxy-1-{4-(cyclopentyloxycarbonyl)-3-methyl-1,3-butanediene-1-yl}-1,2-oxo-2,6,6-trimethylcyclohexane (1g), 312 mg (yield 83%), was obtained in the same manner in Synthesis Example 1 except that 258 mg (3.00 mmol) of cyclopentyl alcohol was used in place of propyl alcohol.

$^1$H-NMR(CDCl$_3$) δ (ppm): 0.96(3H, s), 1.21(3H, s), 1.25 (3H, s), 1.34(1H, dd, J=2.1, 13.7), 1.55~1.63(m), 1.68~1.79 (m), 1.74(1H, d, J=13.7), 1.81~1.93(m), 2.00(3H, d, J=1.2), 2.04(1H, dd, J=2.1, 15.7), 2.27(1H, d, J=15.7), 3.82~3.96 (4H, m), 5.22(1H, m), 5.67(1H, brs), 6.26(1H, dd, J=0.6, 16.0), 7.60(1H, dd, J=0.6, 16.0).

LRMS m/z: 376 (M+).

HRMS m/z: Theoretical, 376.2247 (as $C_{22}H_{32}O_5$); Found, 376.2226

Test Example 1

Effect of Promoting Spinach Growth

Spinach (variety: Aichijiromaru) was seeded in a field and cultivated in a usual manner. At the 4-leaf stage, a mixture of Compound (1e) and gibberellin, or either compound alone was sprayed for treatment. $GA_3$ (commercially available in Japan and used throughout the Examples) and $GA_{4+7}$ (ProVideR, which is commercially available in the US and used throughout the Examples) were tested as the gibberellin.

Thirty five days after spraying, each spinach plant was harvested, and the average individual weights in each group were determined and expressed in percentage terms relative to the untreated group. The concentration used for the spraying treatment and the results are shown in Table 1.

TABLE 1

Effect of promoting spinach growth

| Gibberellin | $GA_3$ | | $GA_{4+7}$ | |
| --- | --- | --- | --- | --- |
| | 5 ppm | 0 | 5 ppm | 0 |
| 1 ppm Compound (1e) | 141.1 | 112.5 | 136.3 | 112.5 |
| 0 ppm Compound (1e) | 114.4 | 100.0 | 116.0 | 100.0 |

Test Example 2

Effect of Promoting Thickening and Growth of a Radish

A radish (variety: Akamaru Comet) was seeded in a field and cultivated in a usual manner. At the 4-leave stage, a mixture of Compound (1e) and gibberellin, or either compound alone were sprayed for treatment. $GA_3$ and $GA_{4+7}$ were tested as the gibberellin.

One month after spraying, each radish was harvested and the average radish root weights in each group were determined and expressed in percentages relative to the untreated group. The concentration used for the spraying treatment and weight results are shown in Table 2.

TABLE 2

Effect of promoting thickening and growth of the radish

| Gibberellin | $GA_3$ | | $GA_{4+7}$ | |
| --- | --- | --- | --- | --- |
| | 10 ppm | 0 | 10 ppm | 0 |
| 1 ppm Compound (1e) | 120.6 | 106.4 | 125.2 | 106.4 |
| 0 ppm Compound (1e) | 105.1 | 100.0 | 106.8 | 100.0 |

Test Example 3

Effect of Promoting Thickening of a Grape

Twenty-year-old grape plants (variety: Kyoho) were tested using regular cultivation techniques. Fifteen days after full blossom, plants were treated with a mixture of Compound (1e) and gibberellin or with either compound alone. During this treatment, plant corollas were immersed therein for 1 to 2 seconds. $GA_3$ and $GA_{4+7}$ were tested as the gibberellin.

Every grape was harvested at the fruit maturity stage. The average fruit weight in each group was determined and expressed as a percentage relative to the untreated group. The gibberellin concentration used for the treatment and the results are shown in Table 3.

TABLE 3

Effect of promoting thickening of the grape

| Gibberellin | $GA_3$ | | $GA_{4+7}$ | |
| --- | --- | --- | --- | --- |
| | 10 ppm | 0 | 10 ppm | 0 |
| 5 ppm Compound (1e) | 121.0 | 108.5 | 125.4 | 108.5 |
| 0 ppm Compound (1e) | 109.2 | 100.0 | 111.7 | 100.0 |

Test Example 4

Effect of Increasing Grains in Paddy Rice
(Increased Ear Weight and Increased Yield)

Paddy rice (variety: Nipponbare) was cultivated in a usual method. At the time of forming young ears, the rice was treated by spraying a mixture of Compound (1e) and gibberellin or either compound alone. $GA_3$ and $GA_{4+7}$ were tested as the gibberellin.

The average number of grains per ear at harvest time was determined and expressed as a percentage relative to the untreated group. The concentration of gibberellin used for the spraying treatment and the results are shown in Table 4.

TABLE 4

Effect on increasing grain weight for paddy rice

| Gibberellin | $GA_3$ | | $GA_{4+7}$ | |
| --- | --- | --- | --- | --- |
| | 10 ppm | 0 | 10 ppm | 0 |
| 0.5 ppm Compound (1e) | 111.8 | 104.7 | 114.7 | 104.7 |
| 0 ppm Compound (1e) | 104.4 | 100.0 | 106.1 | 100.0 |

Test Example 5

Effect of Promoting Petunia Flowering

In late February and in early spring at the 10- to 12-leave stage, petunia plants (variety: Petunia×hybrida Titan) were treated by spraying a mixture of Compound (1e) and gibberellin or either compound alone. $GA_3$ and $GA_{4+7}$ were tested as the gibberellin.

After spraying, plants were cultivated under outdoors conditions. Five plants per treatment group were examined, and the average date for beginning of flowering was determined. The concentration used for the spraying treatment, and the number of days by which flowering was hastened in each group, compared with the average flowering date of the untreated group, are shown in Table 5.

TABLE 5

Effect of promoting flowering of petunia

| Gibberellin | $GA_3$ | | $GA_{4+7}$ | |
| --- | --- | --- | --- | --- |
| | 10 ppm | 0 | 10 ppm | 0 |
| 1 ppm Compound (1e) | 17 | 6 | 21 | 6 |
| 0 ppm Compound (1e) | 7 | 0 | 9 | 0 |

As can be seen from Table 5, petunia flowering was hastened in groups treated with a mixture of Component (1e)

and gibberellin as compared with groups treated with either compound alone.

INDUSTRIAL APPLICABILITY

A plant growth promoter of the present invention comprises a combination of an epoxycyclohexane derivative and gibberellin. The combination causes a strong synergistic action of promoting plant growth over treatment with either compound alone. The combination promotes the growth of stems and leaves, increased yield of grains, promotion of flowering, and thickening of fruits. Accordingly the invention is useful as, for example, a promoter of stem and leaf growth, promoter for fruit thickening, the development of seeds, roots, stems and bulbs, and for promoting flowing.

What is claimed is:

1. A plant growth promoting composition comprising an epoxycyclohexane derivative represented by the general formula:

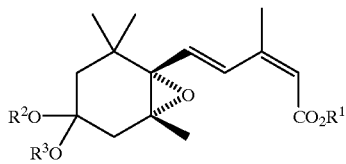

(wherein $R^1$ represents a hydrogen atom, a C1 to C6 alkyl group or a C3 to C6 cycloalkyl group, and $R^2$ and $R^3$ independently are lower alkyl groups or are combined to form a polymethylene group which may be substituted with an alkyl group) and gibberellin as active ingredients.

2. A plant growth promoting composition comprising an epoxycyclohexane derivative according to claim 1, wherein $R^1$ is a propyl group or an isopropyl group and $R^2$ and $R^3$ are combined to form an ethylene group.

3. A method of promoting plant growth comprising applying the composition according to claim 1 onto a plant.

4. A method of promoting plant growth comprising applying the composition according to claim 2 onto a plant.

5. The method of claim 3, wherein the promotion is promotion of growing leaves.

6. The method of claim 3, wherein the promotion is promotion of flowering.

7. The method of claim 3, wherein the promotion is promotion of thickening fruits, seeds, roots, stems or bulbs.

* * * * *